(12) United States Patent
Kenwood et al.

(10) Patent No.: US 12,357,331 B2
(45) Date of Patent: Jul. 15, 2025

(54) DEVICE FOR TISSUE REMOVAL

(71) Applicant: Boston Scientific Scimed Inc., Maple Grove, MN (US)

(72) Inventors: Shannon S. Kenwood, Milford, MA (US); Peter L. Dayton, Brookline, MA (US); Katharine Eckerline, Plymouth, MN (US); Wei Li Fan, San Francisco, CA (US); Douglas Melanson, Natick, MA (US); Mark Bates, Plymouth, MA (US); Gaurav Rohatgi, Waltham, MA (US); Alex Broerman, Somerville, MA (US); Benjamin Peterson, Cambridge, MA (US); Jeff Gray, Sudbury, MA (US); Barry Weitzner, Acton, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 416 days.

(21) Appl. No.: 17/756,207

(22) PCT Filed: Nov. 16, 2020

(86) PCT No.: PCT/US2020/060666
§ 371 (c)(1),
(2) Date: May 19, 2022

(87) PCT Pub. No.: WO2021/101824
PCT Pub. Date: May 27, 2021

(65) Prior Publication Data
US 2022/0346812 A1    Nov. 3, 2022

Related U.S. Application Data

(60) Provisional application No. 62/939,296, filed on Nov. 22, 2019.

(51) Int. Cl.
*A61B 17/221* (2006.01)
*A61B 17/3205* (2006.01)
*A61B 17/00* (2006.01)

(52) U.S. Cl.
CPC ...... *A61B 17/221* (2013.01); *A61B 17/32056* (2013.01); *A61B 2017/00353* (2013.01); *A61B 2017/2212* (2013.01)

(58) Field of Classification Search
CPC .......... A61F 2230/005; A61F 2230/001; A61F 2230/0008; A61F 2230/0058;
(Continued)

(56) References Cited

U.S. PATENT DOCUMENTS

| | | |
|---|---|---|
| 3,791,387 A | 2/1974 | Itoh |
| 5,904,690 A | 5/1999 | Middleman et al. |

(Continued)

FOREIGN PATENT DOCUMENTS

| | | |
|---|---|---|
| CN | 102639068 A | 8/2012 |
| CN | 104739550 A | 7/2015 |

(Continued)

OTHER PUBLICATIONS

International Search Report and Written Opinion issued in International Application PCT/US2020/060666 on Feb. 4, 2021. (10 pages).

*Primary Examiner* — Katherine M Shi
(74) *Attorney, Agent, or Firm* — Bookoff McAndrews, PLLC

(57) ABSTRACT

A medical device that comprises a rim defining a loop in a plane and defining a width measured perpendicular to the plane, at least one wire coupled to a distal end of the rim and extending proximally from the distal end out of the plane to a proximal end of the rim, the at least one wire having a cross-sectional dimension measured perpendicular to a longitudinal axis of the at least one wire, the cross-sectional
(Continued)

dimension being smaller than the width of the rim, and a sheath configured to cover at least a portion of the rim and a portion of the at least one ware.

19 Claims, 6 Drawing Sheets

(58) Field of Classification Search
CPC ............ A61B 17/22031; A61B 17/221; A61B 17/32056; A61B 2017/2212; A61B 2017/00358; A61B 2017/0034; A61B 2017/00867; A61B 2017/22035; A61B 2017/2217; A61B 2017/320064; A61B 17/00234; A61B 17/22; A61B 2017/00287; A61B 2017/320008
See application file for complete search history.

(56) References Cited

U.S. PATENT DOCUMENTS

| | | |
|---|---|---|
| 6,517,551 B1 | 2/2003 | Driskill |
| 8,142,443 B2 | 3/2012 | Saleh |
| 8,206,401 B2 | 6/2012 | Nakao |
| 9,101,383 B1 | 8/2015 | Dostal et al. |
| 2004/0122444 A1* | 6/2004 | Gerard ................ A61B 17/221 |
| | | 606/127 |
| 2009/0030427 A1 | 1/2009 | Razvi et al. |
| 2011/0125181 A1* | 5/2011 | Brady .............. A61B 17/22031 |
| | | 606/200 |
| 2012/0130392 A1 | 5/2012 | Levy et al. |
| 2013/0023894 A1* | 1/2013 | Saleh .................. A61B 17/221 |
| | | 606/113 |
| 2014/0378988 A1 | 12/2014 | Raybin et al. |
| 2016/0242804 A1* | 8/2016 | Fleury ............. A61B 17/32056 |
| 2016/0317165 A1 | 11/2016 | Yokota |
| 2018/0049766 A1 | 2/2018 | Nolan et al. |
| 2019/0159798 A1 | 5/2019 | Saleh |

FOREIGN PATENT DOCUMENTS

| | | |
|---|---|---|
| CN | 105813583 A | 7/2016 |
| CN | 106999197 A | 8/2017 |
| CN | 107735038 A | 2/2018 |
| JP | 2016150044 A | 8/2016 |

* cited by examiner

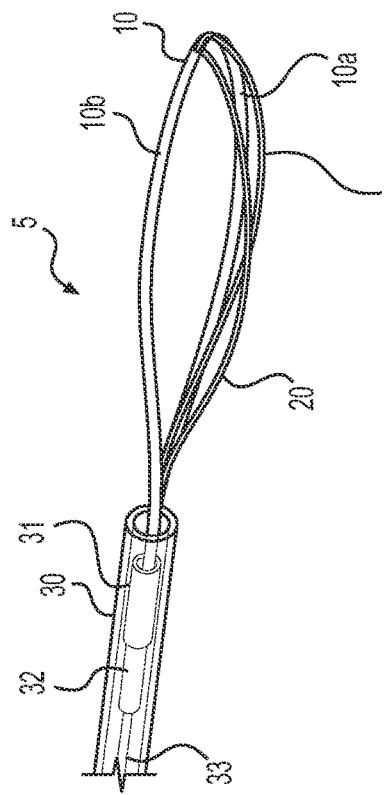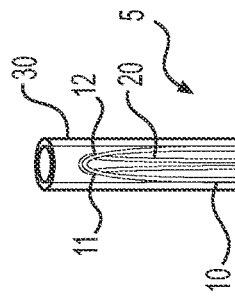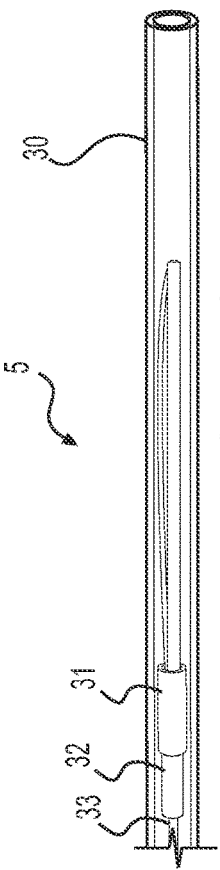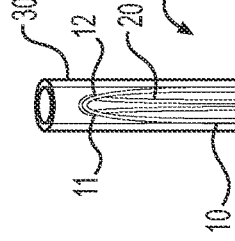

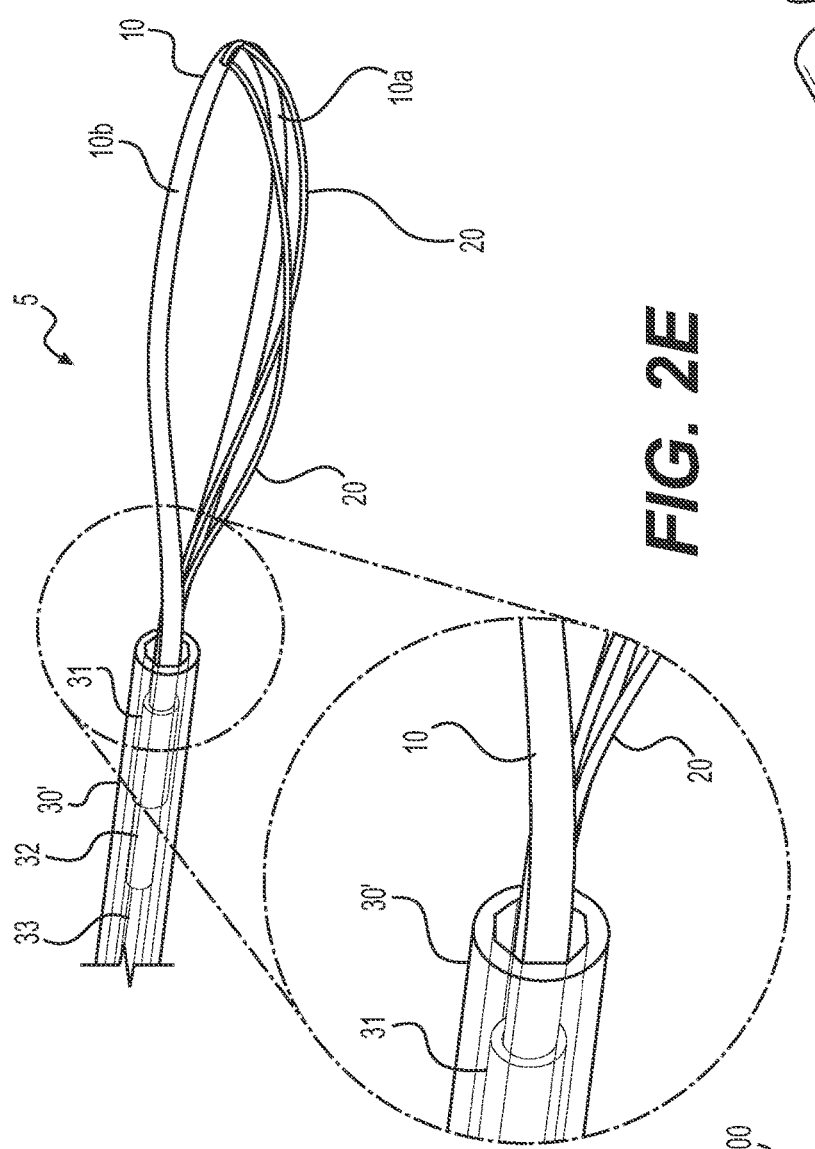
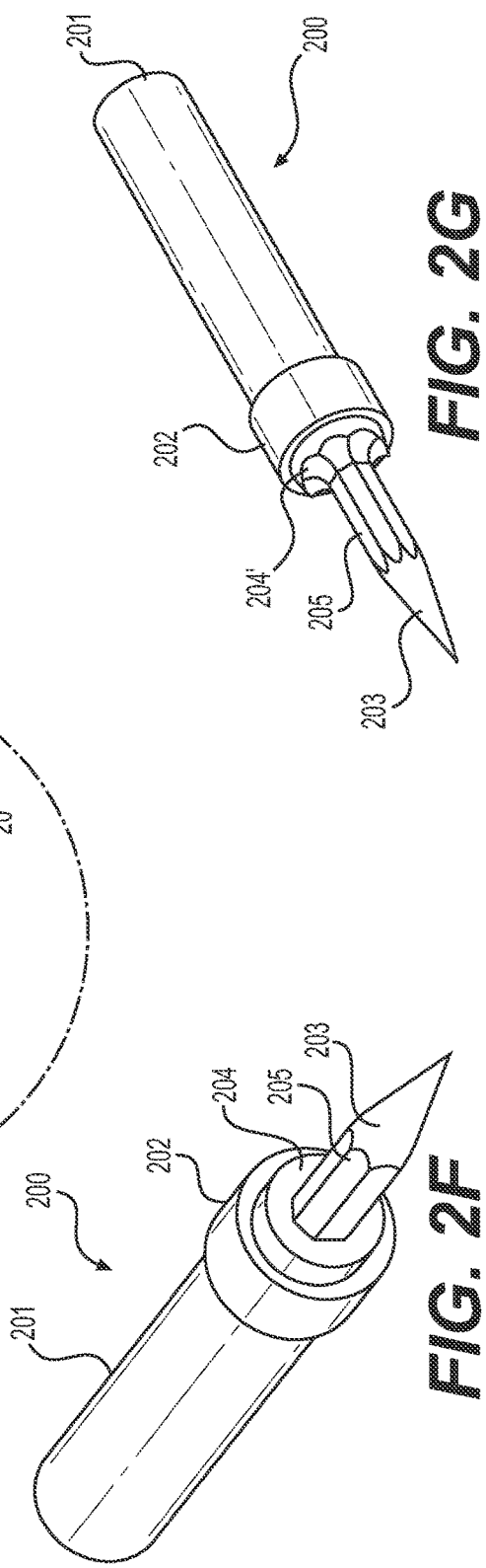

DEVICE FOR TISSUE REMOVAL

CROSS-REFERENCE TO RELATED APPLICATION(S)

This patent application is a National Stage Application of International Patent Application No. PCT/US2020/060666, filed on Nov. 16, 2020, which claims priority to U.S. Provisional Application No. 62/939,296, filed on Nov. 22, 2019, the entirety of which is incorporated herein by reference.

TECHNICAL FIELD

The present disclosure relates generally to removal or retrieval of tissue or other bodily or foreign materials. More particularly, at least some embodiments of the present disclosure relate to a device for endoscopic removal of materials, such as necrotic tissue, from a body cavity, and related methods of using the device.

BACKGROUND

Fluid and necrotic collections, e.g., tissue, can occur as a complication of acute pancreatitis. It has been found that the cavity and infection, when present, resolves more successfully when necrotic tissue is removed. A stent is commonly used to perform a transoral/transmural endoscopic drainage or debridement collection, in which the stent is placed between the collection and the stomach to allow drainage into the stomach. Currently, endoscopic necrosectomy is performed by inserting a scope through the stent and into the cavity having the collection. However, there is no tool designed specifically for this procedure. Standard tools often used may present various issues that limit the efficiency of carrying out this procedure.

SUMMARY OF THE DISCLOSURE

According to an example, a medical device may include a rim defining a loop in a plane and defining a width measured perpendicular to the plane, at least one wire coupled to a distal end of the rim and extending proximally from the distal end out of the plane to a proximal end of the rim, the at least one wire having a cross-sectional dimension measured perpendicular to a longitudinal axis of the at least one wire, the cross-sectional dimension being smaller than the width of the rim, and a sheath configured to cover at least a portion of the rim and a portion of the at least one wire.

In another example, the rim may have a substantially rectangular cross-section. The cross-sectional dimension of the at least one wire may be rectangular and a width of the at least one wire may be less than the width of the rim. The rim may define a thickness measured in the plane, and the thickness may be greater than a thickness of the at least one wire. The rim may include at least one opening at the distal end of the rim, and the at least one wire may extend through the at least one opening. The rim may include two openings at the distal end of the rim, the at least one wire may extend through the two openings, and a portion of the at least one wire may be outside the loop and distal to the rim.

In another example, the medical device may further include at least one actuator. The actuator may be coupled to a proximal end of the rim and/or a proximal end of the at least one wire. The at least one actuator may covered by the sheath. The at least one actuator may also be longitudinally movable relative to the sheath. The at least one actuator may be coupled to both the proximal end of the rim and the proximal end of the at least one wire, thereby extending or retracting the rim and the at least one wire simultaneously via longitudinal movement of the at least one actuator relative to the sheath. The at least one actuator may be multiple actuators, and each of the multiple actuators may be configured to move longitudinally relative to the sheath irrespective of the longitudinal movements of the other multiple actuators.

In another example, the rim of the medical device may be a Nitinol ribbon. The rim may be capable of flexing at least 90° relative to the sheath. The rim may be a continuous curve that is tipless, and an inner surface of the rim may be roughened. The edge of the rim may include serrations or scallops, or is sharp.

In another example, a distal end of the medical device that extends from and retracts into the sheath may consist essentially of the rim and the at least one wire, and the distal end of the device may be rotatable relative to the sheath.

According to an example, a medical device may include a rim defining a loop in a plane, wherein the rim includes at least one opening within a distal end of the rim, and at least one wire coupled to the distal end of the rim and extending out of the plane to a proximal end of the rim, wherein the at least one wire extends through the at least one opening. The medical device may further include a sheath configured to cover at least a portion of the rim and a portion of the at least one wire. The rim may have two openings within the distal end of the rim, wherein the at least one wire extends through the two openings, and wherein a portion of the at least one wire is outside the loop, distal to the rim, and within the plane. The rim may have a substantially rectangular cross-section, and the at least one wire may have a rectangular cross-section.

According to an example, a method of tissue removal may include positioning a medical device including a rim and at least one wire, so that the rim is adjacent the targeted tissue, and removing the targeted tissue from adjacent tissue by capturing the targeted tissue with an edge of the rim. The rim may define a loop in a plane and define a width measured perpendicular to the plane, and the rim may include at least one opening within a distal end of the rim. The at least one wire may be coupled to the distal end of the rim and extend proximally from the distal end out of the plane to a proximal end of the rim. The at least one wire may extend through the at least one opening. The at least one wire may have a cross-sectional dimension measured perpendicular to a longitudinal axis of the at least one wire, and the cross-sectional dimension may be smaller than the width of the rim.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2A is a perspective view of the distal end of the device of FIG. 1A in an extended position out of the sheath.

FIG. 2B is another perspective view of the distal end of the device of FIG. 1A in a slightly retracted position in the sheath.

FIG. 2C is another perspective view of the distal end of the device of FIG. 1A in a fully retracted position in the sheath.

FIG. 2D is an orthogonal view of the distal end of the device of FIG. 1A in a fully retracted position in the sheath.

FIG. 2E is a perspective view of the distal end of a device, including a closer view of the sheath, according to an exemplary embodiment of the present disclosure.

FIGS. 2F-2G are perspective views of different mandrels according to exemplary embodiments of the present disclosure.

DETAILED DESCRIPTION

Figure 1A:
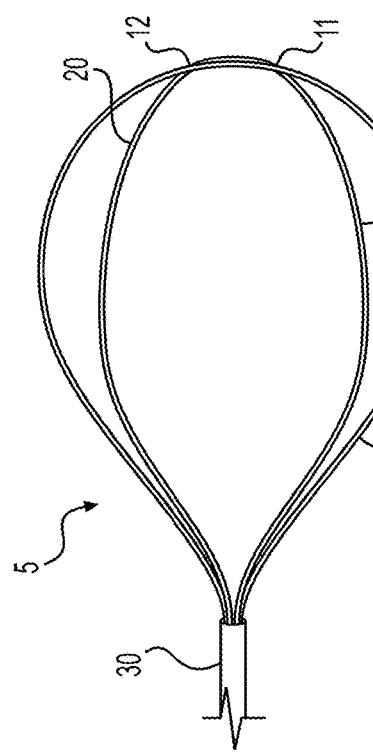
FIG. 1A is a front view of a distal end of a device according to an exemplary embodiment of the present disclosure.
Figure 1B:
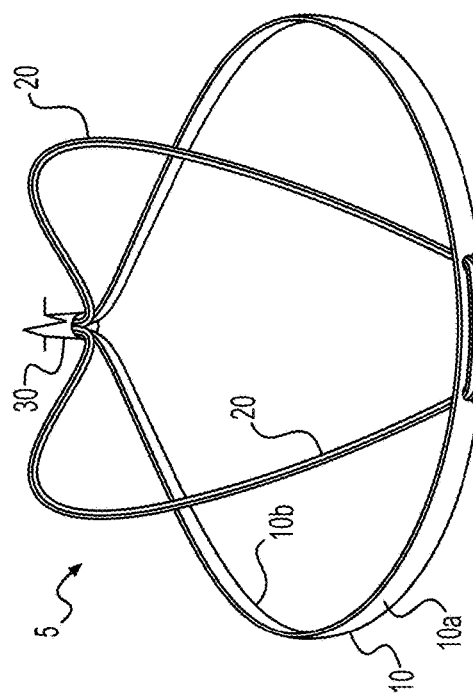
FIG. 1B is a top view of the distal end of the device of FIG. 1A.
Figure 1C:
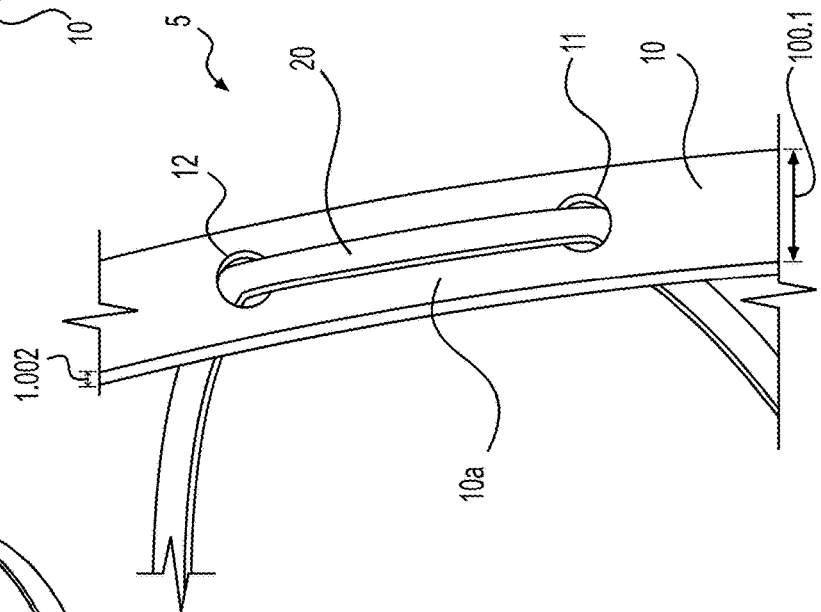
FIG. 1C is a close-up view of the distal end of the device of FIG. 1A.

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

The present disclosure may solve one or more of the limitations in the art. The scope of the disclosure, however, is defined by the attached claims and not the ability to solve a specific problem. The present disclosure is drawn to systems and devices, and related methods, for a tissue removing medical device, among other aspects. It is noted that various embodiments of said medical device may also be used for food impaction, removal of other bodily material, or any foreign body retrieval. Referring to FIGS. 1A-1E, a distal end 5 of a medical device 1 according to an exemplary embodiment is shown. Medical device 1 includes a rim 10, a wire 20, and a sheath 30.

Rim 10 is a wire, cable, or a ribbon made of any suitable biocompatible, flexible material, preferably, Nitinol, which provides excellent thermal shape memory and durability. Rim 10 defines a loop in a plane, a width 1001 that is measured perpendicular to the plane (shown in FIG. 1C), and a thickness 1002 that is measured in the plane (shown in FIG. 1C). The shape of the loop is not particularly limited, and may be, for example, a circle, oval, teardrop, etc. For example, rim 10 may be a single wire with both ends extending to a proximal end of the medical device, forming a loop at a distal end extending from the sheath 30. Rim 10 has a rectangular cross-section, but is not limited thereto in other embodiments. The rectangular cross-section may provide a lateral stiffness to rim 10, which enables the ability to exert lateral force against tissue and help corral said tissue. Rim 10 includes an outer surface 10a of the loop, and an inner surface 10b of the loop. Rim 10 further includes a first opening 11 and a second opening 12 on the distal end of rim 10. In other embodiments, rim 10 may include only one opening, multiple openings, or no opening on the distal end of the rim. The opening or multiple openings may be formed on rim 10 by any suitable manner, preferably, laser drilling. In other embodiments, inner surface 10b of rim 10 may further be sandblasted—either in its entirety or just at the distal end—to roughen inner surface 10b and help prevent or minimize rim 10 from slipping off tougher or firmer tissue. In some other embodiments, rim 10 may be laser cut so that a bottom edge of rim 10 (e.g., the edge facing away from wire 20) includes serrated teeth 13" or scalloped teeth 13' that may be sharp, allowing rim 10 to more easily scrape or remove tougher or firmer tissues, as shown in FIG. 1E. In certain embodiments, rim 10 may flex at least 90° relative to the sheath 30 in any direction (e.g. up/down/left/right), thereby allowing rim 10 to contact and press against tissue and scrape along the surface of said tissue.

Wire 20 may be a ribbon, a wire, a cable, or the like made of any suitable biocompatible, flexible material, preferably, Nitinol. Wire 20 has a cross-sectional dimension measured perpendicular to a longitudinal axis of wire 20, and the cross-sectional dimension is smaller than the width of rim 10. Specifically, wire 20 is flat and has a rectangular cross-sectional dimension. However, wire 20 is not limited thereto, and, in other instances, may have a substantially circular cross-section. The width of the rectangular cross-section of wire 20 is less than the width of rim 10 measured perpendicular to the plane of rim 10, but is not limited thereto in other embodiments. In some embodiments, the thickness of rim 10, measured into the plane, may be greater than the width of the rectangular cross-section of wire 20. For example, a rim 10 may be about 0.5 to about 1 mm wide by about 0.05 to about 0.1 mm thick, or a stiffer rim 10 may be about 0.5 to about 1 mm wide by about 0.05 to about 0.15 mm thick, while wire 20 may have a width from about 0.1 mm to about 0.25 mm. The basket-like configuration of rim 10 and wire 20, further described below, may be about 30 to 35 mm long by about 20 to 25 mm wide and about 5 to 10 mm deep (i.e. measured from the plane of rim 10 to the peak of an arch formed by a strand of wire 20). These dimensions are exemplary only and not restrictive.

Wire 20 is coupled to a distal end of rim 10, by extending through both first opening 11 and second opening 12 of rim 10, so that a portion of wire 20 between the first and second openings 11 and 12 is outside the loop (e.g., along the outer surface 10a) distal to rim 10 and in the plane of the loop. For example, ends of the wire 20 may extend proximally in the device 1, with a single wire 20 forming at least two curvatures out of the plane of the loop of wire 10, forming a basket-like structure. The wire 20 may be threaded through at least first and second openings 20 as a connection point at a distal end of the rim 10. A single wire and distal connection point may be advantageous in reducing manufacturing costs. Furthermore, flat wire 20 may be oriented relative to rim 10 so that wire 20 sits flush against the distal end of rim 10 via any suitable technique, e.g. heat-forming, to minimize any protrusion of wire 20 outside the loop distal to rim 10. As a result of this manner of coupling and wire 20 being flat, rim 10 is a continuous or substantially continuous curve that is an atraumatic distal tip, or in other words, tipless. Thus, when rim 10 is pushed forward into a cavity wall, the pressure applied by device 1 will be low as such pressure or force is spread over a greater surface area, thereby reducing the likelihood of accidentally penetrating the cavity wall as a rim with a sharp or otherwise pronounced tip would.

Wire 20 extends proximally from the distal end of rim 10 out of the plane of rim 10, to a proximal end of rim 10, where sheath 30 covers at least a proximal portion of rim 10 and a proximal portion of wire 20. Thus, two strands of wire 20, arching or curving out of the plane, form a basket-like support in which removed tissue may be retained. Because of the presence of wire 20, in certain embodiments, device 1 does not include any net or net-like or other materials similar in function, e.g., a mesh, a lining, a web, attached to rim 10 to help hold any removed tissue. In other words, no material is between the strands of wire 20 or the loop formed by rim 10, and nothing fills the spaces between them. Wire 20 is only coupled to rim 10 at the proximal end of rim 10, via a heat shrieked tube 31 and a crimp 32, and at the distal end of rim 10, and nowhere else. Thus, device 1 may avoid various limitations associated with the use of a net or net-like or other similarly-functioning materials, including clogging, snagging, and/or ripping, and may cleanly remove the retained tissue from the basket-like support via partial retraction of rim 10 and wire 20 into sheath 30. The geometry of rim 10 and wire 20, the disclosed manner in which rim 10 and wire 20 are coupled together, and the use of Nitinol material help provide a basket-like configuration having a unique ability to perform many high strain cycles without yielding or breakage.

In other embodiments, wire 20 may couple to a distal end of a rim having no opening, or wire 20 may couple to a distal end of a rim having a plurality of openings, by extending through said openings, and thereby resulting in multiple strands of wire 20 extending proximally to form the basket-like shape. In certain embodiments, wire 20 or a plurality of strands thereof only extend proximally from the distal end of a rim to the proximal end of a rim, and not laterally, i.e., side to side of the rim. In certain embodiments, rim 10 may be without wire 20.

Figure 1D:
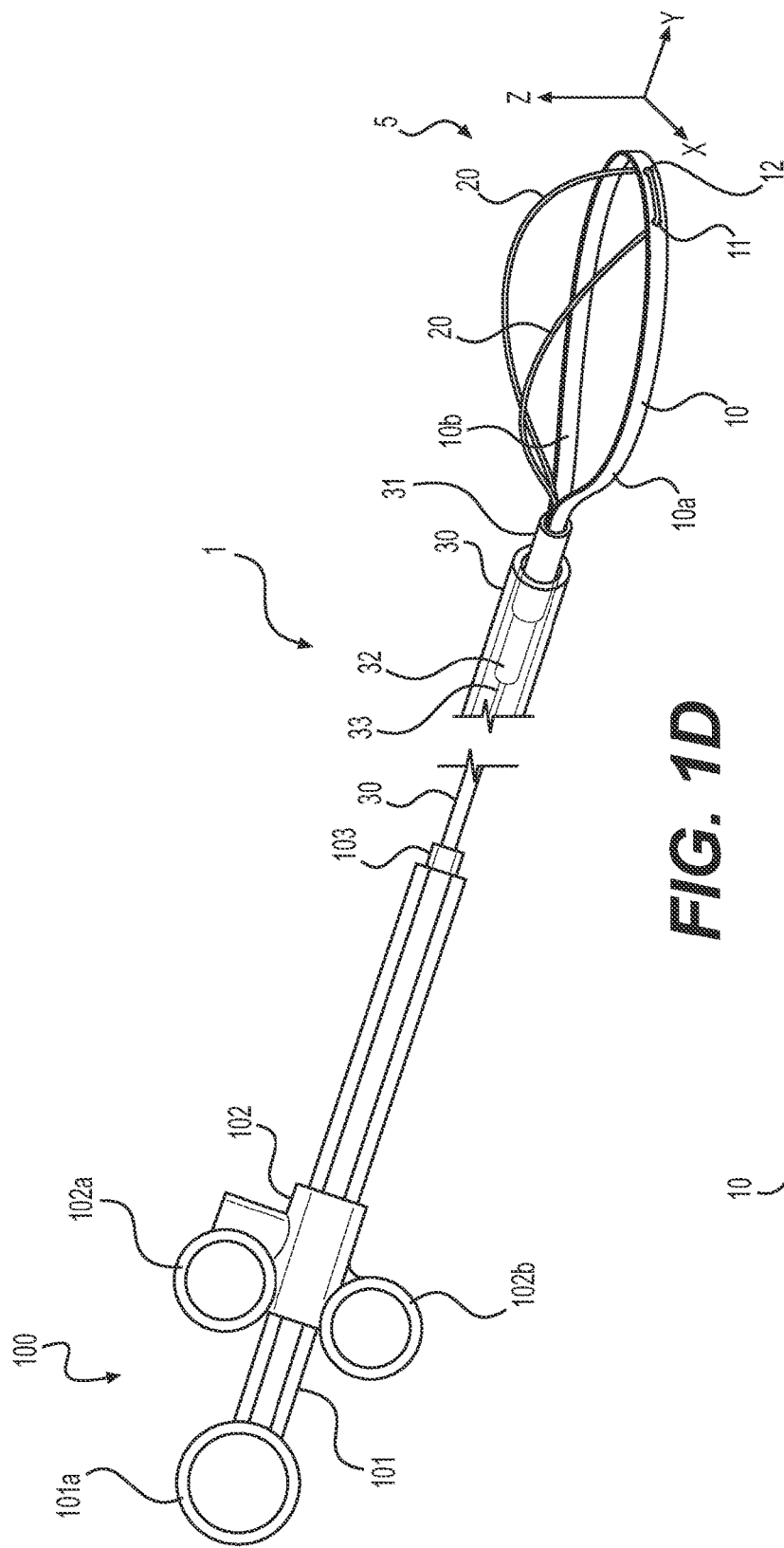
FIG. 1D is a perspective view of a medical device, according to an exemplary embodiment of the present disclosure.
Figure 1E:
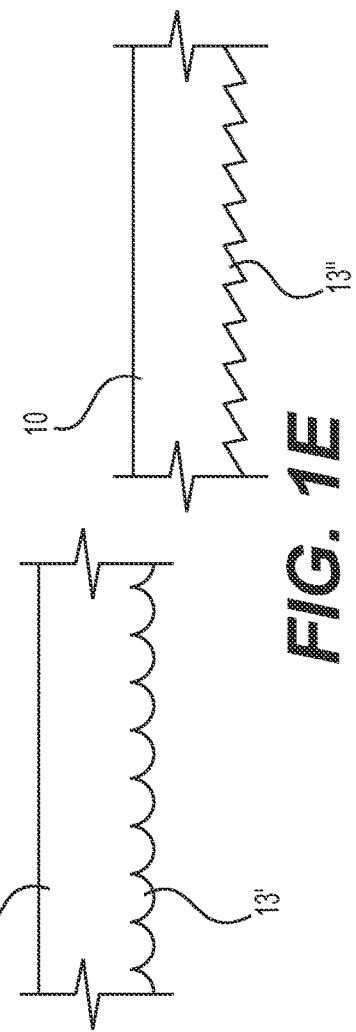
FIG. 1E is a close-up view of a rim of a medical device according to an exemplary embodiment of the present disclosure.

FIG. 1D shows medical device 1, including a controller 100. In this embodiment, sheath 30 covers at least a portion of heat shrinked tube 31, crimp 32, and an actuator 33. Heat shrinked tube 31 covers at least a proximal portion of rim 10 and a proximal portion of wire 20, which may be coupled together in heat shrinked tube 31. The proximal ends of rim 10 and the proximal ends of wire 20 are also crimped and contained in crimp 32, the proximal end of which is connected to actuator 33. Crimp 32, which is a tubular housing, may also house a distal portion of actuator 33, which may be connected to the coupled and crimped proximal ends of rim 10 and wire 20. Crimp 32 may cover all, a portion, or none of heat shrinked tube 31. Heat shrinked tube 31 assists in security of the proximal ends of rim 10 and wire 20, prior to and during the crimping process. Actuator 33 is a flexible wire, a cable, or a plurality (e.g. three) of wires or cables lying adjacent to one another that is longitudinally movable relative to sheath 30.

The proximal end of sheath 30 is connected to a connection point 103 on the distal end of controller 100. Controller 100 further includes a handle 101, which includes a thumb ring 101a, and an actuation control 102, which includes a first finger loop 102a and a second finger loop 102b. Actuator 33 connects to actuation control 102 and may be actuated longitudinally relative to sheath 103 by the longitudinal movement of actuation control 102 relative to handle 101, on which it is held. Thus, actuator 33 may be extended distally by pushing actuation control 102 toward the distal end of handle 101, thereby extending rim 10 and wire 20 simultaneously further out of sheath 30, or actuator 33 may be retracted proximally by pulling actuation control 102 towards the proximal end of handle 101, thereby retracting rim 10 and wire 20 simultaneously further or completely into sheath 30. Thus, the size of the loop of rim 10, as well as the stiffness of said loop, may be controlled by the degree in which rim 10 and wire 20 are extended out of sheath 30. This may allow a user to fully extend rim 10 and wire 20, out of sheath 30, for soft tissue removals, or partially retract rim 10 and wire 20, into sheath 30, for more aggressive removals. The basket-like configuration of rim 10 and wire 20 may also be rotated by rotation of actuator 33 via a mechanism or control (not shown) of controller 100. Such simultaneous extension, retraction, or rotation of rim 10 and wire 20 via a single actuator, i.e., actuator 33, may be referred to as "single action."

FIGS. 2A-2D show the distal end 5 of medical device 1, having rim 10 and wire 20 extended or retracted to varying degrees via single action. In FIG. 2A, rim 10 and wire 20 are in a fully open position, being completely extended out of sheath 30, as a result of actuator 33 being fully extended distally via actuation control 102 (not shown), as described above. In FIG. 2B, rim 10 and wire 20 are in a partially-retracted position, with actuation control 102 (not shown) of controller 100 (not shown) being approximately along the mid-way point of handle 101 (not shown). In the partially-retracted position shown in FIG. 2B, the basket-like support formed by rim 10 and wire 20 may close in around a held tissue to have a better grip thereof. Said tissue may be dispensed or removed from a patient's body by pulling distal end 5 of medical device 1 out of said body altogether, or, more commonly, by fully-retracting the basket of rim 10 and wire 20 and expelling tissue as the basket is retracted. In FIGS. 2C-2D, rim 10 and wire 20 are in fully closed position, being completely retracted into sheath 30, as a result of actuator 33 being fully retracted proximally via actuation control 102 (not shown), as described above. Upon full retraction into sheath 30, rim 10 and wire 20 may cut through the held tissue and eject said tissue cleanly into the stomach from which it will be passed, without having to shake the tissue off or remove the tissue by another way. In some embodiments, the cross-sectional dimensions of rim 10 may be selected with respect to a diameter of sheath 30, such that in a retracted state, e.g., partial or full, a minimum bend radius and internal stress at the distal tip of rim 10 is set for multiple cycles of use.

FIG. 2E shows a medical device similar to the one shown in FIGS. 2A-2D, except sheath 30' differs from sheath 30.

Specifically, the distal opening of sheath 30' is octagonal in shape, unlike the circular opening of sheath 30 (shown in FIGS. 2A-2D). In addition, at least a portion of the inner surface of the sheath defining its lumen and extending proximally from the distal opening has the same octagonal shape. The circumradius of the octagonal distal opening, defined by half the distance between opposite angles of the octagon, may be a distance greater than the width of rim 10. The length of each side of the octagon may be the same as or about the width of rim 10. It is noted that the distal opening of the sheath is not limited to the aforementioned shapes, and, in other embodiments, may have openings of different polygonal shapes, e.g., hexagon, so long as sides of the polygon have a length the same as or about the same as the width of rim 10.

The octagonal distal opening of sheath 30' may help stabilize the basket-like support formed by rim 10 and wire 20, particularly while capturing tissue. For example, in some embodiments, distal end 5 may be free to rotate prior to capturing targeted tissue, so that it may be oriented as needed. After orientation, distal end 5 may be retracted into the sheath to capture tissue within the basket-like support. However, in some instances, distal end 5 may continue to rotate undesirably relative to the sheath, thereby losing or failing to capture the targeted tissue. In contrast, retraction of distal end 5 into the octagonal distal opening of sheath 30' inhibits undesired rotation due to the polygonal shape of the distal opening and the dimensions of its sides matching the width of rim 10. Because of those dimensions, rim 10, when retracted into sheath 30', may catch or engage with inner parallel surfaces of the distal opening, so that rotation is inhibited or at least significantly limited. Thus, sheath 30' may effectively cradle rim 10 as rim 10 is retracted within sheath 30', thereby minimizing unwanted rotation. It is noted that rotation is not inhibited when distal end 5 is extended, since tubular heat shrink 31 is engaging with the distal opening of sheath 30'. Due to its tubular shape, heat shrink 31 is not cradled within the octagonal distal opening of sheath 30' and may rotate freely.

FIGS. 2F-2G show mandrel 200s, which may be used to form the polygonal, e.g., octagonal, distal opening of sheath 30'. Mandrel 200 includes a handle 201, a flange 202, a distal end 204, 204' of handle 201, and an insertion shaft 205. Shaft 205 includes a tapered portion 203 leading to a point. Handle 201 is not particularly limited, and may be any suitable handle-shape that may be grasped. Flange 202 protrudes radially outwards from handle 201, and is found on a distal portion of handle 201. The diameter of flange 202 is not particularly limited, so long as flange 202 serves as a barrier between the remaining, proximal portions of handle 201 and shaft 205. Distal end 204, 204' of handle 201 may be a surface that is flat or shaped. For example, distal end 204 is a flat surface end (shown in FIG. 2F), while distal end 204' is a scalloped surface (shown in FIG. 2G). However, the distal end is not limited thereto, and may have a surface of any suitable shape. Shaft 205 protrudes longitudinally from distal end 204, 204', and is centered about the longitudinal axis of handle 201. Shaft 205 is of a diameter smaller than that of handle 201. More specifically, shaft 205 may be of a diameter that is about the diameter of the distal opening of sheath 30', shown in FIG. 2E. Shaft 205 is multifaceted, and may be polygonal in shape, e.g., octagonal. The length of shaft 205 is not particularly limited. The distal end of shaft 205 tapers downward to a point.

To form the polygonal distal opening of sheath 30', shaft 205 of mandrel 200 may be heated and then inserted into the distal opening of sheath 30'. This may result in the distal opening molding to accommodate the shape of shaft 205, which may be polygonal. Sheath 30', with shaft 205 inserted therein, may then be cooled to set the molded shape of the distal opening of shaft 30'. It is noted that the distal end of sheath 30' may also be molded by inserting shaft 205 within sheath 30' to an extent such that distal end 204, 204' may abut the distal end of sheath 30'. For instance, such insertion of shaft 205 so that distal end 204' contacts the distal end of sheath 30' would result in sheath 30' having a scalloped distalmost end, in accordance with the surface of distal end 204'.

In other embodiments, rim 10 and wire 20 may be extended or retracted independently from one another via the use of multiple actuators, each of which is configured to move longitudinally relative to the sheath irrespective of the movements of the other actuators. This may be referred to as "double action." Referring to FIGS. 3A-3B and FIGS. 4A-4B, another embodiment of medical device 1', having rim 10 and wire 20 extended or retracted to varying degrees via double action, is shown. Device 1' includes rim 10, wire 20, and sheath 30, like the embodiments of FIGS. 1-2C. Sheath 30 covers at least a portion of a rim crimp 32a and a wire crimp 32b, the proximal ends of which are connected to a rim actuator 33a and a wire actuator 33b, respectively. Rim crimp 32a and wire crimp 32b may cover and crimp a portion of the proximal ends of rim 10 and wire 20, respectively. Moreover, rim crimp 32a and wire crimp 32b are independently movable relative to sheath 30 and to each other as well. The proximal ends of rim actuator 33a and wire actuator 33b may be connected to any suitable controller via one or multiple connection points of the controller. For example, each actuator 33a, 33b may be connected to a respective actuation control. As a further example, such actuation control may be like control 102, however, split in two portions that each translates along handle 101.

Figure 3A:
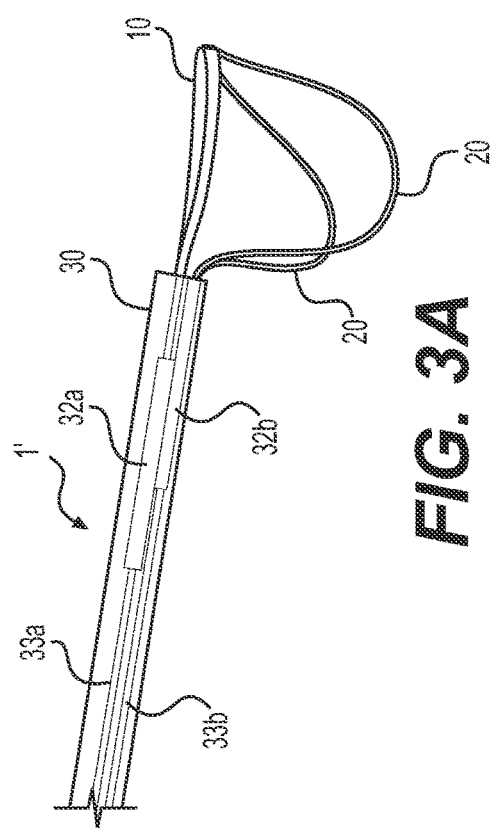
FIG. 3A is a perspective view of a distal end of a device according to another exemplary embodiment of the present disclosure.
Figure 3B:
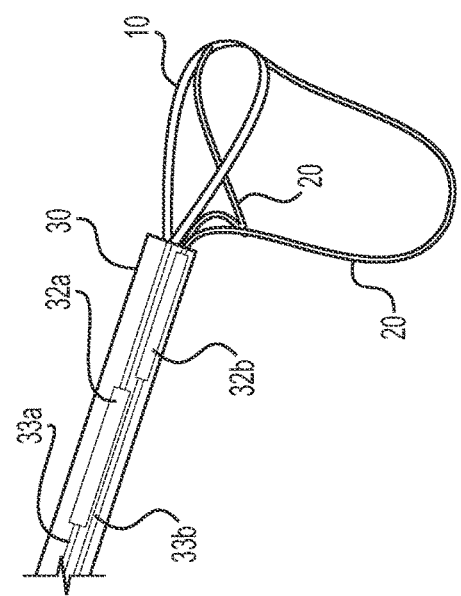
FIG. 3B is another perspective view of the distal end of the device of FIG. 3A in which the rim is further retracted relative to the wire.

In FIG. 3A, rim 10 is retracted towards sheath 30, as a result of rim actuator 33a being retracted proximally, while wire 20 is neither retracted nor extended. Thus, rim crimp 32a is partially-proximal to wire crimp 32b. In FIG. 3B, rim 10 is retracted even further towards sheath 30, as a result of rim actuator 33a being even further retracted proximally, while wire 20 is neither retracted nor extended. Thus, rim crimp 32a is fully proximal to wire crimp 32b. As a result of such double action, the arch or curve of the strands of wire 20 is increasingly pronounced, and the strands of wire 20 are increasingly spaced apart, thereby allowing for easy ejection of removed tissue, without having to completely retract both rim 10 and wire 20 into sheath 30.

Figure 4A:
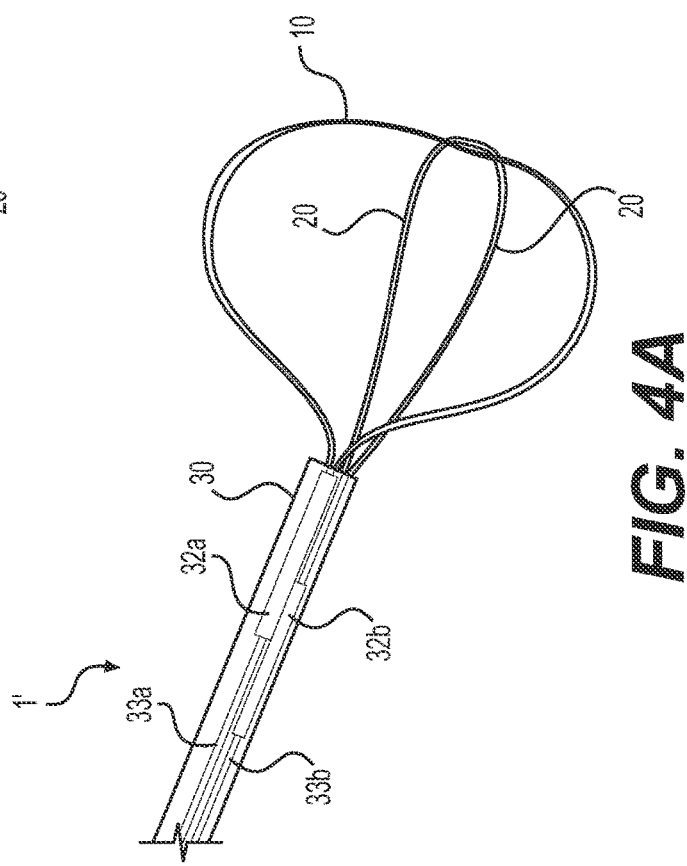
FIG. 4A is a perspective view of a distal end of a device according to an exemplary embodiment of the present disclosure.
Figure 4B:
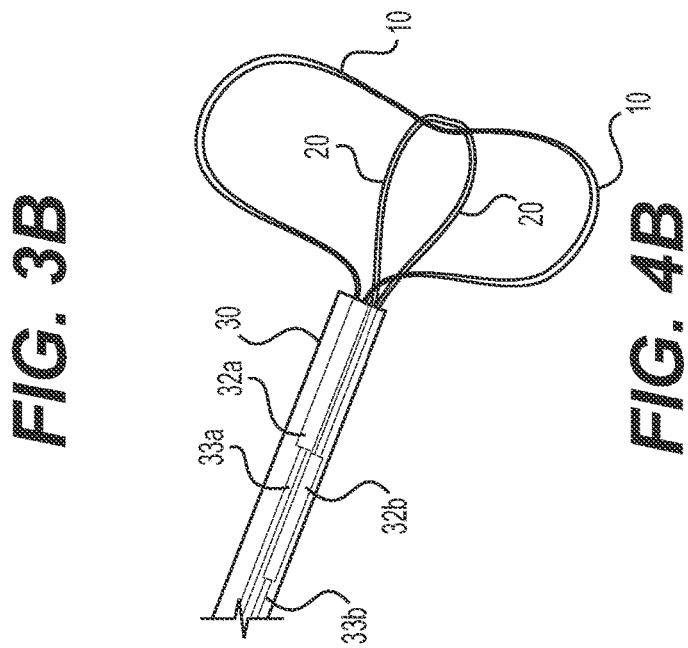
FIG. 4B is another perspective view of the distal end of the device of FIG. 4A in which the wire is further retracted relative to the rim.

In FIG. 4A, wire 20 is retracted towards sheath 30, as a result of wire actuator 33b being retracted proximally, while rim 10 is neither retracted nor extended. Thus, wire crimp 32b is partially-proximal to rim crimp 32a. In FIG. 4B, wire 20 is retracted even further towards sheath 30, as a result of wire actuator 33b being further retracted proximally, while rim 10 is neither retracted nor extended. Thus, wire crimp 32b is fully proximal to rim crimp 32a. As a result of such double action, rim 10 increasingly takes on a kidney bean-shape. In other words, wire 20 pulls proximally on the distal end of rim 10, to which it is coupled, resulting in a distal end of the loop of rim 10 becoming increasingly concave towards the center of the loop. Furthermore, the lateral ends of the loop of rim 10 also further bode out radially. Thus, the double action illustrated in FIG. 4B results in rim 10 forming a kidney bean-like shape, which also allows for easy ejection of removed tissue without having to completely retract both rim 10 and wire 20 into sheath 30. It is noted that in some other embodiments, a third actuator may be further included to separately actuate the rotation of rim 10 and/or wire 20.

Figure 5A:
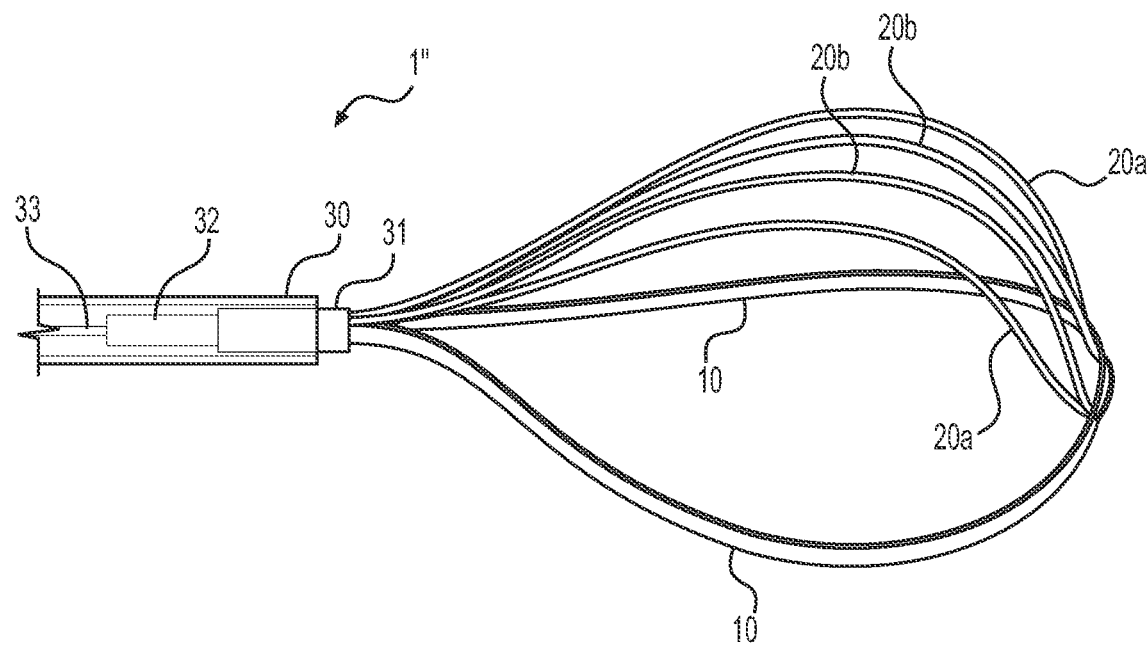
FIG. 5A is a perspective view of a distal end of a device according to another exemplary embodiment of the present disclosure.
Figure 5B:
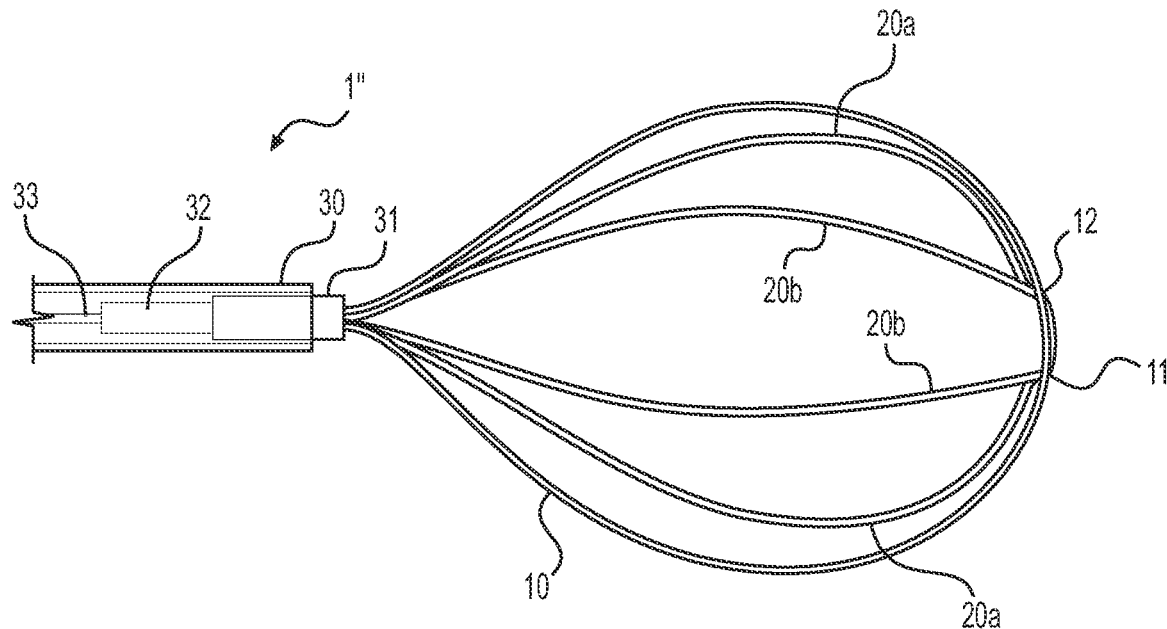
FIG. 5B is another perspective view of the distal end of the device of FIG. 5A.

Referring to FIGS. 5A-5B, another embodiment of medical device 1" including rim 10, a first wire 20a and a second wire 20b, and sheath 30, is shown. Both first wire 20a and second wire 20b are coupled to the distal end of rim 10, by extending both wires through both first opening 11 and second opening 12 of rim 10, in which a portion of first wire 20a and second wire 20b are both outside the loop distal to rim 10, like wire 20 in the embodiment of FIGS. 1-2C. Alternatively, first wire 20a and second wire 20b may extend through separate pairs of in rim 10. First wire 20a and second wire 20b extend proximally from the distal end of rim 10 out of the plane of rim 10, to a proximal end of rim 10, where sheath 30 covers at least a portion of a heat shrinked tube 31, a crimp 32, and an actuator 33, also like the embodiment of FIGS. 1-2C. Heat shrinked tube 31 covers at least a proximal portion of rim 10 and proximal portions of first wire 20a and second wire 20b. The proximal end of rim 10 and the proximal ends of first wire 20a and second wire 20b are crimped and contained in crimp 32, the proximal end of which is connected to actuator 33. Thus, in this embodiment, two strands of first wire 20a and two more strands of second wire 20b, arching or curving out of the plane of rim 10, form a basket-like support in which tissue may be held. As a result of additional strands, more support may be provided to device 1".

An example of a method of removing tissue using any of the embodiments of removal devices illustrated in the Figures is further discussed below. A user may deliver medical device 1, 1', 1" into the body of a subject, e.g., via a natural orifice (such as a mouth or anus) and through a tortuous natural body lumen of the subject, such as an esophagus, stomach, colon, etc. The device may be delivered in any suitable way, for example through a working lumen of an endoscope. A user may direct medical device 1, 1', 1" to an intended target site by various means, including imaging. Once a target site is reached, a user may position device 1, 1', 1" including rim 10 and wire 20, so that rim 10 is over/facing the tissue that is targeted for removal. In other examples, device 1, 1', 1" also be used in an inverted position, so that wire 20 is facing the target tissue, to fragment larger tissue clumps or to help anchor device 1, 1', 1" in position. A user may obtain the targeted tissue by scraping the targeted tissue with rim 10 so that the targeted tissue may be fragmented, dislodged, or removed, and held within the basket-like support formed from rim 10 and wire 20. Rim 10 may flex at least 90° relative to sheath 30 in any direction (e.g. up/down/left/right), thereby allowing rim 10 to press against tissue in this manner and scrape along the surface of said tissue.

A user may also deliver a fluid, e.g. saline, through sheath 30 of device 1, 1', 1", via a connection to an additional port (not shown) a distal end of handle 101. After obtaining the targeted tissue, a user may direct device 1, 1', 1" to an appropriate site for dispensing the tissue, e.g., the stomach, and dispense the tissue. In certain examples, the tissue may be dispensed by retracting rim 10 and wire 20 into sheath 30, via single action or double action, so that rim 10 and wire 20 may cut through the held tissue and eject said tissue. In other examples, the tissue may be dispensed by retracting only rim 10, and not wire 20, via double action, so that the arch or curve of the strands of wire 20 is increasingly pronounced, and the strands of wire 20 are increasingly spaced apart, thereby allowing for the ejection of removed tissue. In other examples, the tissue may be dispensed by retracting only wire 20, and not rim 10, via double action, so that rim 10 increasingly takes on a heart-shape, which allows for the ejection of the removed tissue. In other examples, the tissue may be dispensed by rotating device 1, 1', 1" and allowing for the tissue to fall out of rim 10 simply via gravity. In other examples, the tissue may be held within the basket-like support of distal end 5 of device 1, and distal end 5 may be pulled out of a patient's body altogether to remove said tissue. In other examples, tissue may be removed via suction applied through a channel of an endoscope. Thus, a user, e.g. a physician, may be able to orient device 1, 1', 1", safely grab a significant amount of tissue, remove the tissue cleanly via any method or mechanism, including those described above, and repeat this sequence without device 1, 1', 1" becoming fouled by material, misshapen, or breaking during a procedure.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
   a rim defining a loop in a plane and defining a width measured perpendicular to the plane, wherein the rim has two openings at a distal end of the rim;
   at least one wire coupled to the distal end of the rim and extending proximally from the distal end out of the plane to a proximal end of the rim, the at least one wire having a cross-sectional dimension measured perpendicular to a longitudinal axis of the at least one wire, the cross-sectional dimension being smaller than the width of the rim, wherein the at least one wire extends through the two openings, wherein a portion of the at least one wire is outside the loop and distal to the rim; and
   a sheath configured to cover at least a portion of the rim and a portion of the at least one wire.

2. The medical device according to claim 1, wherein the rim has a substantially rectangular cross-section.

3. The medical device according to claim 1, wherein the cross-sectional dimension of the at least one wire is rectangular, and a width of the at least one wire is less than the width of the rim.

4. The medical device according to claim 3, wherein the rim defines a thickness measured in the plane, wherein the thickness is greater than a thickness of the at least one wire.

5. The medical device according to claim 1, further comprising at least one actuator, wherein the actuator is coupled to a proximal end of the rim and/or a proximal end of the at least one wire, wherein the at least one actuator is covered by the sheath, wherein the at least one actuator is longitudinally movable relative to the sheath.

6. The medical device according to claim 5, wherein the at least one actuator is coupled to both the proximal end of the rim and the proximal end of the at least one wire, thereby extending or retracting the rim and the at least one wire simultaneously via longitudinal movement of the at least one actuator relative to the sheath.

7. The medical device according to claim 5, wherein the at least one actuator is multiple actuators, and each of the multiple actuators is configured to move longitudinally relative to the sheath irrespective of the longitudinal movements of the other multiple actuators.

8. The medical device according to claim 1, wherein the rim is a Nitinol ribbon.

9. The medical device according to claim 1, wherein the rim is capable of flexing at least 90° relative to the sheath.

10. The medical device according to claim 1, wherein the rim is a continuous curve that is tipless.

11. The medical device according to claim 1, wherein an inner surface of the rim is roughened.

12. The medical device according to claim 1, wherein an edge of the rim includes serrations or scallops, or is sharp.

13. The medical device according to claim 1, wherein a distal end of the device that extends from and retracts into the sheath consists essentially of the rim and the at least one wire, and wherein the distal end of the device is rotatable relative to the sheath.

14. A medical device comprising:
a rim defining a loop in a plane and defining a width measured perpendicular to the plane;
at least one wire coupled to a distal end of the rim and extending proximally from the distal end out of the plane to a proximal end of the rim, the at least one wire having a cross-sectional dimension measured perpendicular to a longitudinal axis of the at least one wire, the cross-sectional dimension being smaller than the width of the rim;
a sheath configured to cover at least a portion of the rim and a portion of the at least one wire; and
a plurality of actuators, wherein the plurality of actuators is coupled to a proximal end of the rim and/or a proximal end of the at least one wire, wherein the plurality of actuators is covered by the sheath, wherein each actuator of the plurality of actuators is configured to move longitudinally relative to the sheath irrespective of the longitudinal movements of the other actuators of the plurality of actuators.

15. The medical device according to claim 14, wherein the rim has a substantially rectangular cross-section.

16. The medical device according to claim 14, wherein the rim includes at least one opening at the distal end of the rim, wherein the at least one wire extends through the at least one opening.

17. The medical device according to claim 14, wherein the rim is a Nitinol ribbon.

18. The medical device according to claim 14, wherein the rim is capable of flexing at least 90° relative to the sheath.

19. The medical device according to claim 14, wherein the rim is a continuous curve that is tipless.

* * * * *